United States Patent [19]
Bogosian

[11] Patent Number: 5,932,439
[45] Date of Patent: Aug. 3, 1999

[54] ESCHERICHIA COLI K-12 STRAINS FOR PRODUCTION OF RECOMBINANT PROTEINS

[75] Inventor: Gregg Bogosian, Ballwin, Mo.

[73] Assignee: Monsanto Comapny, St. Louis, Mo.

[21] Appl. No.: 08/748,708

[22] Filed: Nov. 13, 1996

Related U.S. Application Data

[60] Provisional application No. 60/006,672, Nov. 13, 1995.

[51] Int. Cl.$^6$ .............................. C12P 21/02; C12P 1/21
[52] U.S. Cl. ................. 435/69.1; 435/252.1; 435/252.3; 435/252.33; 435/69.4
[58] Field of Search ........................... 435/252.33, 252.3, 435/252.1, 69.1, 69.4

[56] References Cited

U.S. PATENT DOCUMENTS

| | | | |
|---|---|---|---|
| 4,652,630 | 3/1987 | Bentle et al. | 530/344 |
| 4,861,868 | 8/1989 | Krivi | 530/399 |
| 4,985,404 | 1/1991 | Mitchell | 514/6 |

OTHER PUBLICATIONS

Ozenberger, B.A. et al. "Nucleotide sequence of *Escerichia coli* isochorismate synthetase gene entC and evolutionary relationship of isochorismate synthetase to other chorismate–utilizing enzymes" Journal of Bacteriology (Feb., 1989), vol. 171, No. 2, p.

Machida, H. et al. "Studies on the accumulation of orotic acid by *Escherichia coli* K–12" Agricultural Biological Chemistry (1969), vol. 33, No. 6, pp. 868–875.

West, S.E.H. "Isolation of gene involved in iron acquisition by cloning and complementation of *Escherichia coli* mutants" Methods in Enzymology (1994), vol. 235, pp. 363–372.

Jensen, K.F. "The *Escherichia coli* K–12 "wild types" W3110 and MG1655 have an rph frameshift mutation that leads to pyrimidine starvation due to low pyrE expression levels" Journal of Bacteriology (Jun., 1993), vol. 175, No. 11, pp. 3401–3407.

"*Escherichia coli* and *Salmonella typhimurium*: Cellular and Molecualr Biology," (1987) Neidhardt, F.C., et al. (eds.), American Society for Microbiology, vol. 2, chapter 72.

Arnow, L.E. (1937) "Colormetric determination of the components of 3,4–dihydroxyphenyllanine–tyrosine mixtures," *Journal of Biological Chemistry* 118:5310537.

Bryce, G.F. and Brot, N., (1971), *Archives of Biochemisstry & Biophysics,* 142:399–406.

Keshet, E., et al. (1981) *Nucleic Acid Research* 9:19–30.

Machida, H., et al. (1970) *Agr. Biol. Chem.* 34:1129–1135.

O'Donovan, G.A. and Neuhard, J. (1970) *Bacteriological Rev.* 34:278–343.

Schoner, et al. (1984) *Proc. Nat'l Acad. Sci. USA* 81:5403–5407.

Schwartz, M. and Neuhard, J. (1975) "Control of expression of the *pyr* genes in *Salmonella typhimurium*: Effects of variations in uridine and cytidine nucheotide pools." *J. Bacteriol.* 121:814–822.

Shimosaka, M., et al. (1984) *J. Bacteriol.* 160:1101–1104.

Silver, S. and Walderhaug, M. (1992), *Microbiological Reviews* 56:195–228.

Vogel, H.J. and Bonner, D.M. (1956) *J. Biol. Chem.* 218:97–106.

Womack, J.E. and O'Donovan, G.A. (1978), *J. Bacteriol.* 136:825–827.

Wood, D.C., et al. (1984) *J. Biol. Chem.* 264:14741–14747.

*Primary Examiner*—Robert A. Wax
*Assistant Examiner*—Kawai Lau
*Attorney, Agent, or Firm*—Arnold, White & Durkee

[57] ABSTRACT

Novel *Escherichia coli* K-12 strains comprising diminished catechol production and/or orotate phosphoribosyltransferase activity levels of at least about 30 units, and methods for the use of such novel *Escherichia coli* K-12 strains in increasing the production of heterologous proteins therein are disclosed.

24 Claims, No Drawings

ESCHERICHIA COLI K-12 STRAINS FOR PRODUCTION OF RECOMBINANT PROTEINS

This application claims the benefit of provisional application Ser. No. 60/006,672, filed Nov. 13, 1995.

FIELD OF THE INVENTION

The present invention relates to improved *Escherichia coli* K-12 strains and methods for their use in the production of heterologous proteins. In one aspect, the invention relates to the manipulation of *E. coli* K-12 strain genomic DNA such that said genomic DNA comprise novel combinations of specific wild type genes and heterologous genes. In another aspect, the invention relates to novel *E. coli* K-12 strains in which specific wild-type genes are reintroduced into the genomes of *E. coli* K-12 strains lacking said genes. In a further aspect, the invention relates to genetic manipulations of a novel *E. coli* K-12 strain phenotype, which manipulations provide for increased production of heterologous protein therein. In a further aspect, the invention relates to methods for improving the amount of heterologous protein produced in *E. coli* K-12 strains, improving the ability to retrieve said proteins, and for improving the yield of heterologous proteins produced in *E. coli* K-12 strains.

BACKGROUND OF THE INVENTION

With the advent of recombinant DNA technology, the use of microorganisms as mini-factories for the production of many useful proteins, enzymes, and other substances has become a routine occurrence. One broad group of microorganisms of choice for use as mini-factories has included organisms from the genus Escherichia and species *coli* commonly referred to as *E. coli*. Within this group is a widely used subgroup of organisms which are members of a strain referred to as the *E. coli* K-12 strain [see "*Escherichia coli* and *Salmonella typhimurium*: Cellular and Molecular Biology", (1987) Neidhardt, F. C. et al. (eds.), American Society for Microbiology, volume 2, chapter 72].

Individual clones within the *E. coli* K-12 strain are particularly attractive host choices for recombinant DNA (rDNA) manipulations and heterologous protein production due to the many years of research on this strain. This research has established a fairly solid understanding of the genetic, biochemical and physiological characteristics of this strain. Moreover, *E. coli* K-12 strains support the replication of a large number of bacteriophage and plasmids that are potentially useful vectors in heterologous protein production. The intimate knowledge of this strain of bacterium and its compatible vectors have assured its preeminence in recombinant DNA developments. Furthermore, the *E. coli* K-12 strain has been shown to be ineffective in colonizing the human gut or in persisting in any environments outside of laboratory or industrial cultivation, an environmental safety characteristic having both commercial and regulatory significance.

Although the *E. coli* K-12 strain is uniquely different from other *E. coli* strains, it is, in fact, not a single entity. Rather, it is a family of related bacterial clones, all derived by genetic mutation from an original isolate [see "*Escherichia coli* and *Salmonella typhimurium*: Cellular and Molecular Biology" (1987)]. The *E. coli* K-12 strains used for both research and commercial purposes today are derivatives of mutant clones which were created and isolated in the first studies of this strain, using irradiation with X-rays, and later with UV and other chemical treatments to induce random mutations. Some of the genetic mutants or derivatives have evolved through purposeful selection and, thus, have well characterized mutations. It is, however, also recognized that many of the present day derivatives contain undetected and/or, as yet, uncharacterized allelic differences. Thus, present day members of the *E. coli* K-12 strain differ from one another by mutations, both spontaneous and induced, in one or many genes.

The presence of both known and unknown phenotypic characteristics and of known and unknown mutations in the genomes of *E. coli* K-12 strains, however, has deterred neither the use of these microorganisms as host cells for heterologous protein production nor the quest to improve the host cell quality of these microorganisms. For although *E. coli* K-12 strains are currently employed to produce such heterologous proteins as human insulin, growth hormone and the like, the search continues for ways to improve the production of such proteins in these microorganisms. It is of interest to researchers and commercial manufacturers alike to seek improvements in, for example, the overall amount of heterologous protein produced, or reductions in production costs, or increases in the absolute yield of heterologous protein produced in such organisms as *E. coli* K-12.

The novel strains of the present invention and novel methods set forth herein for their use provide for increases in both the amount (level) of heterologous protein produced by *E. coli* K-12 strains and for increases in the yield (amount which can be purified) of heterologous protein. The novel strains and methods of the present invention also provide for production cost savings.

In one aspect, the present invention relates to the correction of a previously known frameshift mutation present in many *E. coli* K-12 strains. Quite surprisingly, correction of this frameshift mutation will result in an increase in the amount and yield of heterologous protein produced in organisms with the corrected mutation and, will furthermore, provide production cost savings.

Specifically, it is known that many *E. coli* K-12 strains have a frameshift mutation in the rph gene (see Jensen, K. F., (1993), *J. Bacteriol.* 175:3401–3407; Womack, J. E. and O'Donovan, G. A. (1978), *J. Bacteriol.* 136:825–827; Machida, H. et al. (1970) *Agr. Biol. Chem.* 34:1129–1135; and Machida, H. and Kuninaka, A. (1969), *Agr. Biol. Chem.* 33:868–875. This frameshift mutation has been demonstrated to affect expression of the downstream pyrE gene resulting in depressed production of the pyrE gene product, phosphoribosyltransferase (ORPTase). Since ORPTase is responsible for the conversion of orotic acid to ortidine monophosphate, depressed levels of ORPTase result in an accumulation of orotic acid in the cell and growth medium during cell growth. Additionally, since ORPTase is an important pyrimidine pathway enzyme, it has been common practice to add uridine, when minimal growth media is used, to avoid possible pyrimidine starvation.

Recent studies by Jensen, K. F. (1993), however, have shown that the addition of uridine to the growth medium of *E. coli* K-12 strains with the rph frameshift mutation has no effect on the overall growth rate (doubling time) of these strains. Jensen, K. F. (1993) has also demonstrated that correction of the rph frameshift mutation in *E. coli* K-12 strains by genetic complementation with fully functional, but genetically unrelated rph and pyrE genes, has no affect on the growth rate (doubling time) of said organisms [see Jensen, K. F., (1993)]. Thus, Jensen teaches that the presence of a rph frameshift mutation is not a growth-limiting defect in *E. coli* K-12 strains. The work of Jensen furthermore strongly suggests that there is no discernable gross metabolic benefit to be obtained by curing or correcting the rph frameshift mutation. Indeed, the work by Jensen seems to specifically demonstrate that the rph frameshift mutation does not create or produce any detectable harmful effects on the growth and reproduction of E. coli K-12 strains containing this frameshift mutation. Additionally, the accumulation of orotic acid, noted in E. coli K-12 strains containing the frameshift mutation, has been shown merely to be an indicator of the presence of the frameshift mutation. Neither Jensen nor others have reported any untoward effects of orotic acid over-production.

It is, therefore, quite surprising, as described in more detail hereinafter, that restoration of a wild-type rph gene in E. coli K-12 strains containing the frameshift mutation can increase the amount of heterologous protein produced in such strains and, furthermore, facilitate the improved purification and yield of heterologous proteins manufactured in these host cells.

SUMMARY OF THE INVENTION

The present invention is directed to novel E. coli K-12 strains useful in increasing the amount and yield of heterologous protein which can be made in E. coli K-12 strains.

In one aspect, the present invention relates to novel E. coli K-12 strains comprising substantially diminished catechol production. In one embodiment, the level of a specific catechol, enterochelin, is diminished by inactivation of the entC gene.

In another aspect, the present invention relates to novel E. coli K-12 strains exhibiting wild-type phosphoribosyltransferase (ORPTase) activity and comprising a heterologous gene.

In yet another aspect, the present invention relates to novel E. coli K-12 strains exhibiting wild-type ORPTase activity and substantially diminished catechol levels. In one embodiment, the genomes of such E. coli K-12 strains comprises a wild-type rph gene and an inactive entC gene.

In still another aspect, the present invention relates to improved methods for heterologous protein production in E. coli K-12 strains comprising employing the novel strains of the present invention.

DETAILED DESCRIPTION OF THE INVENTION

The present invention relates to novel E. coli K-12 strains which are selected or created by purposeful genetic alteration of bacterial clones within the E. coli K-12 strain. The term "E. coli K-12 strain" is understood to include the culture Escherichia coli (strain E. coli K-12) from the collection of the bacteriology department at Stanford University and all derivatives thereof including mutants, spontaneous and induced, thereof, mutants isolated after irradiation with X rays, UV irradiation and/or other treatments, chemical or genetic, and clones or further derivatives thereof [see e.g. "Escherichia coli and Salmonella typhimurium: Cellular and Molecular Biology", (1987)]. E. coli K-12 strains can be obtained from the "E. coli Genetic Stock Center" at Yale University, New Haven, Conn.

The present invention also relates to the production of heterologous proteins in E. coli K-12 strains. The term "heterologous" is understood to mean, not naturally occurring within or not native to the specified host cell. When used herein to describe a protein or protein sequence, the term heterologous includes, for example, proteins which are not naturally produced by a specific microorganism or cell, synthetic or otherwise non-naturally occurring proteins, and/or sequences thereof, and any protein sequence which is purposefully manipulated to achieve a non-naturally occurring level or activity within a defined host cell or microorganism.

The term "heterologous" may sometimes also be used herein to describe a genetic element(s) such as a gene, nucleic acid (DNA or RNA) sequence, plasmid or chromosomal fragment. When used herein to describe such a genetic element, the term heterologous is understood to include, for example, native DNA sequences inserted at alternate sites in the host genome; native DNA sequences which have been amplified, deleted or mutated; and DNA sequences not naturally contained within the specific cell of interest which sequences may be isolated from the same or different strain, species, genus, order or class of organism or are synthetic equivalents or variants thereof.

When describing the specific genetic alterations employed to create the novel E. coli K-12 strains of the present invention, reference will be made to the "genomes" or "genetic composition" of these organisms. The term "genome" or "genetic composition" is understood to mean the entire genetic matter, both structural and functional, which is inheritable and/or otherwise transferable, and is contained within an identified cell or microorganism. The genome (genetic composition) of a microorganism is thus understood to include both chromosomal DNA and extra-chromosomal DNA (e.g. plasmids, R factors and the like).

It is further understood by those of skill in the art that the introduction of novel or heterologous DNA into the genomes of E. coli K-12 strains, or the creation of site-specific mutations in the genomes of E. coli K-12 strains can be accomplished by conventional recombinant DNA methodologies exemplified by those methods set forth in "Current Protocols in Molecular Biology" (1995 updated edition), F. Ausubel et al. (eds.), published by John Wiley & Sons, incorporated by reference herein. Furthermore, expression of heterologous DNA sequences can be achieved by conventional methodologies using publicly available promoters, ribosome binding sites, signal sequences (when appropriate or desired), translation stop signals, enhancer sequences, and the like, in accordance with the methods set forth in Methods in Enzymology, (1990), volume 185, David W. Goeddel, Editor, Academic Press, Inc., incorporated by reference herein.

When referring to the "level" or "amount" of heterologous protein produced in a given bacterial host cell, the "level" or "amount" is understood to mean a quantitative measure of protein present or detectable, in accordance with the method of production selected, in the cell culture. For example, if the method of heterologous protein production chosen results in an accumulation of heterologous protein within the cell itself, then the level or amount of heterologous protein produced will be that quantitative measure of heterologous protein present with the cells themselves. If the method of heterologous protein production involves secretion of the protein, then the level of protein production will be that quantitative measure of heterologous protein present in the growth medium.

When referring, herein, to the "yield" of heterologous protein, the term "yield" is understood to mean a quantitative amount of an essentially pure heterologous protein, which protein is retrieved and/or purified essentially free from proteins naturally associated with the host strain. In ascertaining a quantitative "yield" or "amount" of heterologous protein produced by a bacterial host cell, such as *E. coli* K-12 strains, conventional protein-specific methods such as immunoassay, high performance liquid chromatography (HPLC), enzymatic activity, spectrophotometric techniques and the like can be employed.

One aspect of the present invention relates to novel manipulations of a new, not yet reported, phenotypic characteristic in the *E. coli* K-12 strain. The novel *E. coli* K-12 phenotype comprises an unregulated overproduction or accumulation of catechols, such as enterochelin. Said overproduction is manipulated, as described hereinafter, to substantially diminish the production and accumulation of catechols by such *E. coli*.

Enterochelin, also called enterobactin, is a member of the iron scavenging class of compounds termed catechols. Enterochelin is produced by many microorganisms, such as *E. coli*, in response to low free iron levels in the growth environment. Thus, when free iron concentrations are low, catechols such as enterochelin are synthesized. Conversely, when free iron concentrations in the medium or growth environment are high, no detectable levels of catechols such as enterochelin are produced by *E. coli*. This iron-dependent regulation of catechol production in *E. coli* can be demonstrated by showing a positive correlation between the free iron concentration in, for example, the growth medium, and the level of bacterial growth at which production (derepression) of catechols occurs. This positive correlation can, typically, be demonstrated up until such point at which bacterial growth can either not be measured or has stopped [see Bryce, G. F., and N. Brot, (1971), *Archives of Biochemistry & Biophysics*, 142: 399–406].

*E. coli* K-12 strains, for an as yet unexplained reason, continue to produce catechols such as enterochelin in the presence of iron concentrations normally sufficient to prevent derepression of the enterochelin biosynthetic pathway. This absence of iron-dependent feedback inhibition results in an accumulation of catechols in the cell and growth medium. Catechol production or accumulation can be ascertained by the method described by Arnow, L. E., (1937), *Journal of Biological Chemistry* 118: 531–537, incorporated by reference hereto. By combining conventional analytical means, available to those of skill in the art, for determining bacterial growth with means such as those described by Arnow, L. E. (1937) for determining the presence of catechols, one can easily identify *E. coli* K-12 strains which overproduce catechols such as enterochelin (e.g. lack iron-dependent regulation of catechol production).

The loss or absence of iron-dependent feedback inhibition of catechol production in *E. coli* K-12 strains is particularly evident when these organisms are grown in a chemostat and is most often observed under high cell density growth conditions. Indeed, in some chemostat-grown cultures of *E. coli* K-12 strains, iron dependent feedback inhibition of catechol production can be observed at lower cell densities only to be lost when these same cultures are grown at high cell densities.

In one embodiment, an *E. coli* K-12 strain, useful in the present invention, is shown to exhibit an iron-dependent repression/inhibition of catechol production at optical densities of less than about 20 in the presence of about 80 to about 90 micromolar iron. At culture optical densities greater than about 20, catechol production is no longer suppressed even when grown in media containing as much as about a 1000 micromolar free iron concentration.

As previously stated, one aspect of the present invention relates to novel manipulations of this new phenotypic anomaly. In one embodiment, *E. coli* K-12 strains which exhibit unregulated catechol production, or accumulation thereof, are purposefully manipulated to cause a reduction in catechol production, or accumulation, in these organisms. In a specific embodiment, the biosynthetic processes involved in the production of catechols by the strain are manipulated to cause a significant diminution in the detectable level of catechols produced irrespective of the free iron concentration in the growth environment. Catechol production can be said to be significantly diminished when less than about four (4) micrograms of catechols per milliliter of culture are detected, in accordance with the method originally described by Arnow, L. E. (1937) and as set forth in Example 2, hereinafter, irrespective of the free iron concentration in the growth environment. *E. coli* K-12 strains of the present invention which have been successfully manipulated to exhibit substantially diminished catechol production are hereinafter said to be "catechol inhibited".

In a preferred embodiment, significant diminution in catechol production is effected by interrupting at least one gene controlling enterochelin biosynthesis, uptake or regulation. In *E. coli*, enterochelin biosynthesis, uptake across the outer and inner cell membranes, and regulation are controlled by a cluster of 14 genes, arranged in seven transcriptional units. These genes and recent progress in the understanding of the synthesis and the functioning of enterochelin in *E. coli* is comprehensively reviewed by Silver, S. and Walderhaug, M. (1992), *Microbiological Reviews* 56: 195–228. This article is hereby incorporated by reference hereto. For purposes of the present invention, the cluster of 14 genes described therein is referred to as the "ent operon". Interruption of enterochelin biosynthesis, uptake and/or regulation can be accomplished by inactivating one or more genes in the ent operon.

The specific inactivation of one or more genes within the ent operon can be accomplished by any number of conventional methodologies. For example, site-specific mutations can be introduced into selected genes within the ent operon, a gene within the operon or portion of said gene can be deleted, heterologous DNA can be inserted into selected genes within the ent operon, control of expression of a gene(s) within the ent operon can be rendered temperature-sensitive or sensitive to some other external factor. The foregoing manipulations or mutations can be conducted or induced by such conventional means as homologous recombination, transposon mutagenesis or chemical mutagenesis and the like as generally described in Miller, J. H. (ed.), (1991), *Methods in Enzymology*, Volume 204, "Bacterial Genetic Systems", Academic Press, New York, incorporated herein by reference hereto. The measurable result of such a metabolic interruption or genetic manipulation is the absence of detectable catechol production or a significantly diminished catechol production by the target (e.g. manipulated) strain.

When employing any of the foregoing gene inactivation methodologies, it is preferable that any targeted interruption or inactivation be accompanied by some selectable means or marker so that the modified *E. coli* K-12 strain clone can be more easily identified and isolated. Examples of selectable markers useful in the genetic manipulations of the present invention include antibiotic resistance genes and those described in Miller, J. H. (ed.) (1991), incorporated by reference herein.

In a preferred embodiment, the gene or genes of choice for interruption or inactivation within the ent operon are those responsible for enterochelin biosynthesis. Interruption or inactivation of the biosynthetic genes provides for an inactivation of the enterochelin cycle at an early step in the cycle. Such an early interruption is desirable to avoid a possible accumulation of other cyclic intermediates. The genes involved in enterochelin biosynthesis include entC, entB, entA, entD, entE, entF, and entG. Any one or combination of these genes are preferably inactivated.

In a most preferred embodiment of the present invention, interruption of enterochelin biosynthesis is accomplished by inactivating the first gene in the biosynthetic pathway, the entC gene. Inactivation of the entC gene may be achieved by insertion therein of a selectable, heterologous gene or by any other gene-inactivation technique. In one example, an antibiotic resistance gene is inserted into the entC gene using conventional homologous recombination techniques as follows.

A kanamycin resistance gene is isolated by the polymerase chain reaction (PCR) from an E. coli strain containing a copy of the transposon Tn5, which includes a gene encoding resistance to kanamycin. The PCR is also used to amplify a segment of E. coli K-12 chromosomal DNA of approximately 750 bp containing a portion of the entC gene of E. coli. The PCR fragment containing the kanamycin resistance gene is ligated to the 750 bp fragment containing a portion of the entC gene in such a manner as to flank the kanamycin resistance gene with entC sequences. The resulting ligation products are used to transform an E. coli K-12 strain with selection for kanamycin resistance. The resulting kanamycin resistant strain will contain the kanamycin resistance gene of Tn5 inserted by homologous recombination into the entC gene. Further identification or verification of entC inactivation, e.g. isolation of "enterochelin inactivated" or "catechol diminished" E. coli K-12 clones, can be made by demonstrating the clone's inability to obtain normal growth densities on iron depleted media, or inability to produce detectable amounts of catechols when grown in iron-limited medium, or production of substantially diminished amounts of catechols, or by nucleotide sequencing of the altered entC gene.

In another aspect, the present invention relates to the use of the foregoing novel catechol diminished E. coli K-12 strains to produce heterologous proteins. Quite surprisingly, these novel E. coli K-12 strains are shown to be particularly useful in obtaining increased levels of heterologous protein produced therein, increased yields of such heterologous proteins, and a decreased cost of production for such proteins when compared to otherwise identical E. coli K-12 strains which exhibit unregulated overproduction of enterochelin. While the exact cellular or metabolic mechanism responsible for the observed increase in the level of heterologous protein production is not known, I believe that the observed increases in amount and yield of heterologous protein produced, and reduction in the cost of producing said proteins, is due to a diminished presence or absence of catechol production in these cells. Specifically, I have determined that a reddish brown coloration, observable in the cell pellets of E. coli K-12 strains exhibiting unregulated catechol production, is due, in part, to enterochelin accumulation in these cells. Furthermore, a similar discoloration can be found in a thick precipitate which accumulates on columns such as DEAE-cellulose used during heterologous protein purification. This thick precipitate ultimately causes a costly, premature destruction of the useful life and function of said columns and can interfere with protein yields. Thus, by significantly diminishing the production and accumulation of catechols, such as enterochelin, in the E. coli K-12 host bacterium in accordance with the methods of the present invention, the level of heterologous protein production can be increased, the ultimate yield of heterologous protein can be increased, and the cost of production reduced.

In one embodiment, a preferred E. coli K-12 strain which exhibits enhanced heterologous protein production upon inactivation of its entC gene is strain W3110. E. coli strain W3110 is available from the American Type Culture Collection (ATCC), 12301 Parklawn Drive, Rockville, Md., 20852, U.S.A., under the ATCC accession number 27325 and the "E. coli Genetic Stock Center" at Yale University. Examples of heterologous proteins which can be expressed in such E. coli K-12 strains as strain W3110 include human and animal growth factors, somatotropins, plant proteins, and any other heterologous peptide or protein for which an expression system is operable in E. coli. Operable expression systems typically include the conventional gene expression components set forth in Methods in Enzymology, volume 185, (1990). When using such conventional expression systems in E. coli K-12 host cells, the heterologous proteins produced in the host cells can be synthesized as fusion proteins, secreted into the media or into the periplasmic space, produced in free form in the cytoplasm, or accumulated in intracellular bodies such as in inclusion bodies. Purification of the heterologous proteins similarly involves the use of aforementioned conventional, publicly available methodologies which are adapted, again by conventional techniques, to the protein of interest.

In one embodiment, the heterologous protein selected for production in such catechol inhibited E. coli K-12 host cells is bovine somatotropin ("BST"). Vectors comprising a gene able to cause expression of BST or a variant thereof in E. coli and useful in the present invention include those published by Krivi, G. G. in U.S. Pat. No. 4,861,868 issued Aug. 29, 1989; E. Keshet et al. (1981) Nucleic Acid Research 9: 19–30; and Schoner et al. (1984) Proc. Nat'l. Acad. Sci. U.S.A. 81:5403–5407, all incorporated by reference herein. These publications also provide examples of conventional methods of E. coli transformation and methods for determining the levels of heterologous protein production in E. coli. When a catechol inhibited E. coli K-12 strain is transformed with a vector comprising a heterologous gene such as that encoding BST and are grown under conditions which promote expression of BST in these host cells, a significant increase in BST accumulation is achieved as compared to BST accumulation levels in E. coli K-12 strains which accumulate catechols. Similar increases in the total yield of BST in catechol inhibited E. coli K-12 strains can also be noted. See Wood, D. C. et al. (1984) J. Biol. Chem. 264: 14741–14747, and Bentle, et al. U.S. Pat. No. 4,652, 630, issued Mar. 24, 1987, all incorporated herein by reference hereto, for examples of methods useful in purifying BST essentially free from E. coli host cells.

In another aspect, the present invention relates to novel E. coli K-12 strains, the genomes of which comprise a heterologous DNA sequence and a wild-type rph gene, and, thus wild-type levels of ORPTase activity. It has been previously demonstrated that a frameshift mutation in the rph gene of E. coli K-12 strains has a polar effect on the expression of the pyrE gene, located downstream of rph, with a resultant low level of orotate phosphoribosyltransferase and accumulation of orotic acid. E. coli K-12 strains with the rph frameshift mutation produce orotate phosphoribosyltransferase with a specific activity of about 5–20 units, while other E. coli strains with a wild-type rph gene exhibit orotate phosphoribosyltransferase (ORPTase) specific activity levels of about 30–90 units when employing the method originally described by Schwartz, M. and Neuhard, J., (1975), J. Bacteriol. 121:814–822, and set forth in Example 1 hereinafter. I have found that by employing *E. coli* K-12 strains which exhibit wild-type ORPTase levels as host cells for heterologous protein production, I can increase the level of heterologous protein production in *E. coli* K-12 strains. Furthermore, as described more fully hereinafter, these strains also provide for an increased yield of heterologous protein produced therein and, thus, a decreased cost of heterologous protein production.

While the precise mode of action for the observed increase in the levels of heterologous protein produced in rph wild-type containing *E. coli* K-12 strains is not known, measurable increases in the yield of heterologous proteins produced and reduced costs of production in such hosts are believed to be due to the following. As stated previously, *E. coli* K-12 strains containing the rph frameshift mutation accumulate orotic acid. I have found that said accumulation interferes with the isolation and purification of heterologous proteins produced therein. Specifically, I have found that excess orotic acid forms a waxy precipitate that precludes conducting various precipitation steps in the cold. It is desirable to use reduced temperatures to inhibit proteolytic degradation of heterologous proteins produced in bacteria, such as *E. coli*, by proteolytic enzymes naturally present in these organisms. The waxy precipitate created by excess orotic acid also interferes with solubilization of cell pellets and various protein separation columns routinely employed in the retrieval of the heterologous proteins from their bacterial host factories. Thus, by significantly diminishing orotic acid accumulation in *E. coli* K-12 cultures employed to produce heterologous proteins, the yield of these proteins can be significantly increased and the cost of obtaining the proteins reduced.

In one embodiment of the present invention, novel *E. coli* K-12 strains, the genomes of which comprise a heterologous DNA sequence and a wild-type rph gene, are created by first selecting an *E. coli* K-12 strain that possesses a wild-type rph gene. Examples of *E. coli* K-12 strains possessing the wild-type rph gene include *E. coli* K-12 Q13 and *E. coli* K-12 30(E+) [see Machida & Kuninaka (1969) *Agr. Biol. Chem.* 33:868–875]. Additional *E. coli* K-12 strains possessing a wild-type rph gene and/or exhibiting wild-type levels of ORPTase activity can be readily identified by determining the level of ORPTase activity in cultures of the selected *E. coli* K-12 strains, by sequencing the rph-pyrE operon contained therein.

Once an *E. coli* K-12 strain comprising a wild-type rph gene and/or exhibiting wild-type levels of ORPTase activity is identified, a heterologous gene encoding a desired heterologous protein, and able to cause expression of said protein in *E. coli*, is inserted therein by conventional transformation methodologies. The resultant novel *E. coli* K-12 strains, comprising the novel combination of a heterologous gene and wild-type ORPTase activity, are then cultured under conditions which allow for expression of the heterologous gene and production of the protein encoded therein, and the desired protein is then purified.

Typically, *E. coli* K-12 strains containing an rph frameshift mutation exhibit from about 5 to about 20 units of ORPTase as compared to about 30 to about 90 units of ORPTase when employing the enzymatic assay originally described by Schwartz, M. and Neuhard, J. (1975) and as set forth in Example 1, herein below. Thus, "significantly diminished orotic acid accumulation" can be said to occur when ORPTase activity exceeds about 30 units. The nucleotide sequence of an rph gene containing a frameshift mutation is set forth by Jensen, K. F. (1993). Additionally, the nucleotide sequence of the wild-type rph/pyrE operon is available from the GenBank/EMBL data bank under accession numbers X00781 and X01713, and the sequence of the intercistronic rph-pyrE segment and the flanking regions is available from the EMBL data bank under accession number X72920. It is also understood by those of skill in the art that, when referring to wild-type rph and pyrE DNA sequences, such sequences include natural or synthetic sequences which are functionally equivalent to those published and deposited, and any synthetic or endogenous DNA sequences isolated or constructed from such microorganisms as *E. coli* and *Salmonella typhimurium* [see Womak, J. E. and O'Donovan, G. A. (1978) *J. Bacteriol.* 136:825–827] and *Serrata marcescens, Pseudomonas aeruginosa* and *Neurospora* [see O'Donovan, G. A. and Neuhard, J., (1970), *Bacteriological Rev.* 34:278–343]. It is further understood by those of skill in the art that the foregoing rph and pyrE sequences not only provide sequence information useful for determining rph and pyrE genetic abnormalities, but are also a source of wild-type rph and pyrE gene sequences for the rph frameshift mutation correction methodologies of the present invention.

In another embodiment, the novel *E. coli* K-12 strains of the present invention are created by first selecting *E. coli* K-12 strains possessing a rph frameshift mutation or for organisms possessing mutations in the pyrE gene [see Shimosaka, M. et al. (1984) *J. Bacteriol.* 160: 1101–1104] and then "correcting" the mutation. In a preferred embodiment, *E. coli* K-12 strains possessing a rph frameshift mutation are selected from the following group of *E. coli* K-12 strains: *E. coli* K-12 strain CR63, *E. coli* K-12 strain K, *E. coli* K-12 strain W33450, *E. coli* K-12 strain W3623, *E. coli* K-12 strain 594, *E. coli* K-12 strain IAM1264, *E. coli* K-12 strain F$^+$Sm'$^r$, and *E. coli* K-12 strain W3110 [see Machida, H. and Kuninaka, A. (1969) *Agr. Biol. Chem.* 33: 868–875 ] and those *E. coli* K-12 strains within the W3110 pedigree [see "*Escherichia coli* and *Salmonella typhimurium*: Cellular and Molecular Biology", (1987). Alternatively, *E. coli* K-12 strains possessing a rph frameshift mutation or mutation in the pyrE gene can be identified by measuring the level of ORPTase activity or by DNA sequence analysis of the pyrE and/or rph genes.

In a preferred embodiment, the rph frameshift mutation in *E. coli* K-12 strains such as W3110 is corrected as follows. Screening by orotate phosphoribosyltransferase enzyme assay of a number of *E. coli* K-12 strains identified one, *E. coli* K-12 wild-type strain CGSC #5073 (which can be obtained from the "*E. coli* Genetic Stock Center", stock #5073, Yale University, New Haven, Conn.), with a wild-type rph gene. This wild-type rph gene can be introduced into *E. coli* K-12 strains in the following manner. The *E. coli* K-12 strain SO6355 [Jensen, K. F. (1993)], which contains a kanamycin resistance gene inserted into the pyrE gene, is used as the donor in a P1-mediated cross with the strain containing the rph frameshift mutation, with selection for kanamycin resistance. The resulting kanamycin resistant strain is then used as the recipient in a cross with the *E. coli* K-12 wild-type strain CGSC #5073 as the rph wild-type donor, with selection for pyrimidine prototrophy. The resulting strain can be shown by orotate phosphoribosyltransferase enzyme assay or nucleotide sequencing to contain a wild-type rph gene.

It is preferred that the wild-type rph gene be obtained from an *E. coli* K-12 strain, as opposed to another strain of *E. coli* or some other genus or species of bacteria, so that any additional DNA inevitably introduced into the recipient *E. coli* K-12 strain during the recombination event is of the same genetic background. Use of an *E. coli* K-12 strain possessing a wild-type rph gene as a source thus preserves the integrity of the *E. coli* K-12 strain genotype. Said "reconstituted" or "corrected" hosts can then be transformed or genetically engineered, by conventional techniques, to produce the heterologous protein of commercial or other interest.

The successful introduction of the wild-type rph gene into *E. coli* K-12 strains previously containing the frameshift mutation is verified by the presence of an ORPTase specific activity of at least about 30 units, as measured by the enzymatic assay method described by Schwartz, M. and Neuhard, J. (1975) and described in Example 1 herein below. *E. coli* K-12 strains containing a wild-type rph gene are hereinafter referred to as "rph wild-type containing *E. coli* K-12 strains" or "rph corrected *E. coli* K-12 strains". Once corrected, these rph corrected *E. coli* K-12 strains are transformed with a gene encoding and capable of expressing a heterologous protein to create the novel *E. coli* K-12 strains of the present invention and useful in increasing the level of heterologous protein produced therein, useful in reducing the cost of production and useful in increasing the yield of heterologous protein produced thereby.

In one embodiment of the present invention, an rph corrected *E. coli* K-12 strain is transformed with a vector comprising an expressible porcine somatotropin (PST) gene in accordance with the methods described by Krivi, G. G. in U.S. Pat. No. 4,861,868 issued Aug. 29, 1989. In this embodiment, a statistically significant increase in the level of PST is seen as compared to levels of PST produced by an otherwise identical *E. coli* K-12 strain comprising a rph frameshift mutation. As with the observed increase in heterologous protein production in entC inactivated *E. coli* K-12 strains described above, rph wild-type containing *E. coli* K-12 strains can facilitate increases in heterologous protein production independent of the means by which the host cell is engineered to produce, secrete and/or accumulate said heterologous proteins.

Use of *E. coli* K-12 strains comprising ORPTase specific activity levels of greater than about 30 units, in accordance with the methods of the present invention, also increases the yield of heterologous proteins produced therein and reduces the cost of heterologous protein production thereby.

In yet another aspect, the present invention relates to the creation and use of novel *E. coli* K-12 strains which possess ORPTase specific activity levels of greater than about 30 units and which exhibit a diminished production of catechols in low iron containing growth environments. Quite unexpectedly and quite surprisingly, the presence of both of the foregoing traits in *E. coli* K-12 strains provides a synergistic increase in the production of heterologous proteins in such *E. coli* K-12 strains. Specifically, by employing *E. coli* K-12 strains which exhibit diminished catechol accumulation and diminished orotic acid accumulation, a statistically significant increase in the level of such heterologous proteins as PST can be achieved. Attendant increases in the yield and thus a decrease in the cost of production can also be achieved.

In a preferred embodiment, a rph corrected *E. coli* K-12 strain is manipulated, in accordance with the methods of the present invention, to inactivate the entC gene. The resultant novel *E. coli* K-12 strains comprising a corrected (e.g. wild-type) rph gene and inactivated entC gene are then selected for transformation with a vector comprising a heterologous protein such as PST. The transformants are then grown under conditions which promote heterologous protein production. Quite surprisingly, the level and yield of heterologous protein produced by these novel *E. coli* K-12 strains exceeds the sum of the increase in level and yield observed when *E. coli* K-12 strains comprising either an entC inactivated gene or rph corrected gene are employed.

The following examples illustrate preferred embodiments of the present invention and are not intended to limit the scope of the invention in any way. While this invention has been described in relation to its preferred embodiments, various modifications thereof will be apparent to one skilled in the art from reading this application.

EXAMPLE 1

The following example describes an enzymatic assay useful in determining the specific activity of ORPTase in cultures of *E. coli* K-12 strains. This assay is as essentially described by Schwartz, M. and Neuhard, J. (1975) "Control of expression of the pyr genes in *Salmonella typhimurium*: Effects of variations in uridine and cytidine nucleotide pools." *J. Bacteriol.* 121: 814–822, in which the enzyme orotate phosphoribosyltransferase (ORPTase) is referred to as "OMPppase".

All bacterial growth media and specialty chemical components are obtained from either Sigma Chemical Co. (St. Louis, Mo.) or Difco Laboratories (Detroit, Mich.).

The starting cultures for the assay are 10 milliliters (ml) of fresh overnight cultures in L-broth. The 10 ml L-broth starting cultures are used to directly inoculate one liter shake flasks of Vogel-Bonner minimal medium (200 mg/l $MgSO_4$-$7H_2O$, 2 g/l citric acid monohydrate, 10 g/l anhydrous $K_2HPO_4$, 3.5 g/l $NaNH_4HPO_4$-$4H_2O$, and 5 g/l glucose [Vogel, H. J. and D. M. Bonner (1956) *J. Biol. Chem.* 218: 97–106]. After 7–8 hours of growth, the cells are harvested for assay by centrifugation at 1500 g for 10 minutes at 4° C. The cell pellets are resuspended in 20 ml of cell extraction buffer (100 mM Tris, 2 mM EDTA, pH 7.6). The proteins are extracted from the cells by sending each cell suspension through an Aminco French pressure cell. Each extract is centrifuged at 9000 g for 10 minutes at 4° C. One ml aliquots of the protein extract are placed in tubes and either assayed immediately, or frozen at −80° C. until assayed. The protein concentrations in the extracts are determined with a Bio-Rad (Hercules, Calif.) protein assay kit in accordance with the manufacturer's instructions.

To assay for orotate phosphoribosyltransferase activity, 50 mg of orotic acid (monopotassium salt) are dissolved in 10 ml of Pyrimidine Enzyme Assay Starter Buffer (100 mM Tris, 6 mM magnesium chloride, pH 8.8). This orotic acid solution is diluted by adding 1 ml of it to 9 ml of Pyrimidine Enzyme Assay Starter Buffer. This is the 10× solution of orotic acid. Separately, 20 mg of 5-phospho-α-D-ribosyl-1-diphosphate are dissolved in 5 ml of Pyrimidine Enzyme Assay Starter Buffer. This is a 10× solution of 5-phospho-α-D-ribosyl-1-diphosphate. One test tube for each assay is used, plus one test tube for a control. In each test tube are placed 8 ml of Pyrimidine Enzyme Assay Starter Buffer. To this buffer is added 1 ml of the 10× solution of orotic acid, and 100 μl of protein extract. For the control tube, the protein extract is omitted. The assay is started by adding 1 ml of the 10× solution of 5-phospho-α-D-ribosyl-1-diphosphate to each tube. The control solution is used as a blank to zero a UV spectrophotometer at 295 nm. Then the absorbance at 295 nm of each assay tube is determined, and this absorbance is recorded as the time zero reading. The sample tubes are placed in a 37° C. waterbath. At periodic intervals, the absorbance at 295 nm of each assay tube is determined.

The assay and the calculation of activity are based on the fact that when the enzyme orotate phosphoribosyltransferase converts orotic acid and 5-phospho-α-D-ribosyl-1-diphosphate to the nucleotide orotidine 5'-monophosphate (also called OMP, or orotidylic acid), the loss of orotate can be measured as a drop in absorbance at 295 nm. A decrease in absorbance at 295 nm (and in a 1 cm light path) of 3.67 is equivalent to the conversion of 1 μmole of orotate per ml of reaction. The following formula yields the specific activity of orotate phosphoribosyltransferase in units which are defined as nanomoles of orotate consumed per minute per mg of protein:

$$\frac{\text{(drop in absorbance units at 295 nm)} \times (1000\ \text{nmole}) \times (1000\ \mu g/mg)}{(3.67) \times (\mu g\ \text{protein in 1 ml of reaction}) \times (\text{reaction time in minutes})}$$

$$( = )\ \text{nmole/min} - \text{mg}$$

The drop in absorbance units at 295 nm is calculated by subtracting the absorbance reading at 295 nm of each reaction tube at the completion of the reaction from the time zero absorbance reading at 295 nm of each reaction.

Note that the formula calls for the number of μg of protein in each 1 ml of reaction; the reactions are actually in a volume of 10 ml, so that if (for example), one had determined the protein concentration of the sample to be 1.7 mg/ml and had added 100 μl (170 μg of protein) of this solution to each 10 ml reaction tube, that would equal 17 μg of protein in a 1 ml reaction, and the number 17 would be used in the formula.

EXAMPLE 2

The following example demonstrates a method useful in determining the accumulation or production of catechols by bacteria such as E. coli K-12 strains and is conducted essentially in accordance with the method of Arnow, L. E. 1937. "Colorimetric determination of the components of 3,4-dihydroxyphenylalanine-tyrosine mixtures." J. Biol. Chem. 118: 531–537.

Samples of bacterial cultures, grown as described in the preceding example, are centrifuged at 10,000 g for 5 minutes to pellet the cells, and the resulting supernatants are assayed. Each sample to be assayed is adjusted to a volume to 2.0 ml with distilled water. To each tube of sample is added 2.0 ml of 0.5 N hydrochloric acid, followed by 2.0 ml of sodium nitrite/sodium molybdate solution (10 g of sodium nitrite and 10 g of sodium molybdate per 100 ml of distilled water) and 1.0 ml of 2.0 N sodium hydroxide. The samples are incubated at room temperature for 5 minutes. The absorbance of each sample at 516 nm is determined spectrophotometrically, and compared to the absorbance of a set of standards (comprised of 2,3-dihydroxybenzoic acid dissolved in distilled water) to determine the concentration of catechols in each sample.

EXAMPLE 3

This example demonstrates a method useful in substantially diminishing catechol production in E. coli K-12 strains. Specifically, this example sets forth a method for inactivating the entC gene in E. coli K-12 strains.

Four primers were purchased from Midland Reagent Co. (Midland, Tex.).
Primer Kan-1 had the sequence:

5'-CCGTTCTCTTGCTCGAGGCCACCACATTCCGC (SEQ ID NO:1)

and the primer Kan-2 had the sequence:

5'-CGCGAAGTATCCAGCTCGAGTGGGTGGTGAGC (SEQ ID NO:2).

Both primers contained a cleavage site (CTCGAG) for the restriction endonuclease XhoI. Primer Ent-Eco-1 had the sequence:

5'-GCACTAGTGAATTCCCGGCTGTGAACGGGG ATTCGCCCG (SEQ ID NO:3) and the primer Ent-Eco-2 had the sequence:

5'-GCGTTTTCTTGCGAATTCGCTTTACCTTCA AAGGG (SEQ ID NO:4).

Both of these primers contained a cleavage site (GAATTC) for the restriction endonuclease EcoRI. Primers Kan-1 and Kan-2 can be used in a polymerase chain reaction (PCR) to amplify a segment of Tn5 of approximately 2400 bp containing the kanamycin resistance gene of Tn5. Primers Ent-Eco-1 and Ent-Eco-2 can be used in a PCR to amplify a segment of E. coli K-12 chromosomal DNA of approximately 750 bp containing a portion of the entC gene of E. coli.

Chromosomal DNA from E. coli K-12 strain PLK1278 (which can be obtained from the "E. coli Genetic Stock Center", stock #6388, Yale University, New Haven, Conn.), which contains a copy of Tn5 inserted into the chromosome, was used as the template in a PCR with primers Kan-1 and Kan-2 to produce the 2400 bp fragment containing the kanamycin resistance gene. Chromosomal DNA from E. coli K-12 strain W3110 (available from the American Type Culture Collection (ATCC), 12301 Parklawn Drive, Rockville, Md., 20852, U.S.A., under the ATCC accession number 27325), which contains a wild-type copy of the entC gene, was used as the template in a PCR with primers Ent-Eco-1 and Ent-Eco-2 to produce the 750 bp fragment containing a portion of the entC gene.

The 2400 bp fragment containing the kanamycin resistance gene was digested with XhoI, and the resulting overhanging ends were filled in with Klenow DNA polymerase. The 750 bp fragment containing a portion of the entC gene was digested with EcoRI and then ligated to itself to produce closed circular DNA molecules. These circular DNA molecules were then digested with EcoRV, and this material was mixed with the blunt-ended 2400 bp fragment containing the kanamycin resistance gene and ligated. The resulting ligation products were used to transform E. coli K-12 strain JC7623 (which can be obtained from the Coli Genetic Stock Center, stock #5188, Yale University, New Haven, Conn.), with selection for kanamycin resistance. One such kanamycin resistant strain was retained and designated strain LBB398. Strain LBB398 was used as the donor in a P1-mediated cross with strain W3110 (available from the American Type Culture Collection (ATCC), 12301 Parklawn Drive, Rockville, Md., 20852, U.S.A., under the ATCC accession number 27325), with selection for kanamycin resistance. The resulting kanamycin resistant strain was designated strain LBB400. Strain LBB400 contains the kanamycin resistance gene of Tn5, on a 2400 bp fragment of DNA, inserted into the EcoRV site within the entC gene.

Production of BST, and variants thereof, in such entC inactivated E. coli K-12 strains as LBB400, resulted in BST levels of from about 7 to 8 grams of BST per liter of culture as compared to about 5 to 6 grams per liter of BST in the unaltered E. coli K-12 strain.

EXAMPLE 4

This example describes a method useful in correcting the rph frameshift mutation.

A frameshift mutation in the rph gene of E. coli K-12 strains has a polar effect on the expression of the pyrE gene, located downstream of rph, with a resultant low level of orotate phosphoribosyltransferase and accumulation of orotic acid. I found that E. coli K-12 strains with the rph frameshift mutation produce orotate phosphoribosyltransferase at levels of about 5 to about 20 units, and most typically at levels of about 10 units, while other E. coli strains with a wild-type rph gene produce orotate phosphoribosyltransferase at levels of at least about 30 to about 90 units and most typically at levels of about 50 units when the assay method described in Example 1, above, is employed.

Screening by orotate phosphoribosyltransferase enzyme assay of a number of E. coli K-12 strains identified one, E. coli K-12 wild-type strain CGSC #5073 (which can be obtained from the "E. coli Genetic Stock Center", stock #5073, Yale University, New Haven, Conn.), with a wild-type rph gene. This wild-type rph gene was introduced into E. coli K-12 strain W3110 (available from the American Type Culture Collection (ATCC), 12301 Parklawn Drive, Rockville, Md., 20852, U.S.A., under the ATCC accession number 27325) in the following manner. The E. coli K-12 strain SO6355 [described in Jensen, K. F.(1993)], which contains a kanamycin resistance gene inserted into the pyrE gene, was used as the donor in a P1-mediated cross with strain W3110, with selection for kanamycin resistance. The resulting kanamycin resistant strain was designated strain LBB404. The E. coli K-12 wild-type strain CGSC #5073 (which can be obtained from the Coli Genetic Stock Center, stock #5073, Yale University, New Haven, Conn.), with a wild-type rph gene, was then used as the donor in a P1-mediated cross with strain LBB404, with selection for pyrimidine prototrophy. The resulting strain, designated LBB405, was shown by orotate phosphoribosyltransferase enzyme assay to contain a wild-type rph gene.

Production of PST, or variants thereof, in such a rph corrected E. coli K-12 strain as LBB404 resulted in an increase in PST production. Specifically, PST levels increased to about 7 to 8 grams per liter from the about 5 to 6 grams per liter seen in E. coli K-12 strains comprising a rph frameshift mutation.

EXAMPLE 5

This example describes a method useful in creating an E. coli K-12 strain comprising diminished catechol production and ORPTase levels of at least about 30 units. More specifically, this example demonstrates a method for creating an E. coli K-12 strain comprising an inactive entC gene and a wild-type rph gene.

Both genetic alterations, namely the inactivated entC gene and the restoration of the rph gene to a wild-type sequence, were combined in the following manner. Strain LBB398 (described in Example 3, above) was used as the donor in a P1-mediated cross with strain LBB405 (described in Example 4, above), with selection for kanamycin resistance. The resulting kanamycin resistant strain was designated strain LBB406. Strain LBB406 contains both the inactivated entC gene and the restoration of the rph gene to a wild-type sequence. Nucleotide sequencing of both loci in strain LBB406 confirmed that the strain contained both genetic alterations.

Production of PST, or variants thereof, in such an E. coli K-12 strain as LBB406 showed a significant increase in the levels of PST produced. Specifically, levels of from about 9 to 10 grams of PST per liter were obtained in the genetically altered E. coli K-12 strain as compared to PST production levels of about 5 to 6 grams per liter in the unaltered E. coli K-12 strain.

What is claimed:

1. An *E. coli* K-12 strain in which catechol production has been significantly diminished by inactivation of the ent operon, said strain comprising a gene encoding a heterologous plant or animal protein wherein said protein is produced at a higher level than in an *E. coli* K-12 strain in which the ent operon has not been inactivated.

2. The *E. coli* of claim 1 wherein the heterologous protein is a somatotropin.

3. The *E. coli* of claim 2 wherein the somatotropin is a bovine somatotropin.

4. The *E. coli* of claim 1 in which the inactive ent operon comprises an entC gene having inserted therein a heterologous DNA sequence encoding a selectable marker.

5. The *E. coli* of claim 4 wherein the selectable marker is an antibiotic resistance gene.

6. The *E. coli* of claim 5 wherein the antibiotic is kanamycin.

7. The *E. coli* of claim 6 wherein the heterologous protein is a somatotropin.

8. The *E. coli* of claim 7 in which the somatotropin is a bovine somatotropin.

9. An *E. coli* K-12 strain derived from an *E-Coli* K-12 strain mutant for the rph gene, wherein the genome of said derived strain has been modified to contain a wild type rph gene and a gene encoding a heterologous plant or animal protein, wherein said protein is produced at a higher level than in an *E. coli* K-12 strain in which the wild type rph gene is not present.

10. The *E. coli* of claim 9 wherein the heterologous protein is a somatotropin.

11. The *E. coli* of claim 10 wherein the somatotropin is a porcine somatotropin.

12. The *E. coli* of claim 9 wherein the strain comprises a wild type rph gene and exhibits an orotate phosphoribosyltransferase specific activity of at least about 30 units.

13. An *E. coli* K-12 strain comprising an ORPTase specific activity of at least 30 units and exhibiting significantly diminished catechol production.

14. The *E. coli* of claim 13 wherein said *E. coli* is an *E. coli* K-12 strain, naturally mutant for the rph gene, the genome of said strain comprising a wild type rph gene.

15. The *E. coli* of claim 14 comprising an entC gene which has been inactivated.

16. The *E. coli* of claim 15 wherein the inactivated entC gene comprises a gene encoding kanamycin resistance.

17. The *E. coli* of claim 16 further comprising a gene encoding and able to cause the expression of a somatotropin.

18. The *E. coli* of claim 17 wherein the somatotropin is a porcine somatotropin.

19. In a method for producing a heterologous protein in an *E. coli* K-12 strain, the improvement comprising employing an *E. coli* K-12 strain selected from the group consisting of the strains of claims 1, 9, or 13.

20. The method of claim 19 wherein the heterologous protein is a somatotropin.

21. The method of claim 20, wherein the somatotropin is a bovine somatotropin or a porcine somatotropin.

22. In a method for producing a heterologous protein in an *E. coli* K-12 strain, the improvement comprising employing an *E. coli* K-12 strain selected from the group consisting of the strains of claims 4, 5, 6, 14, 15, and 16.

23. The method of claim 22, wherein the heterologous protein is a somatotropin.

24. The method of claim 23, wherein the somatotropin is a bovine somatotropin or a porcine somatotropin.

\* \* \* \* \*

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 32 base pairs
      (B) TYPE: nucleic acid
      (C) STRANDEDNESS: single
      (D) TOPOLOGY: linear (xi) SEQUENCE DESCRIPTION: SEQ ID NO:1:

CCGTTCTCTT GCTCGAGGCC ACCACATTCC GC    32

(2) INFORMATION FOR SEQ ID NO:2:

(i) SEQUENCE CHARACTERISTICS:
      (A) LENGTH: 32 base pairs
      (B) TYPE: nucleic acid
      (C) STRANDEDNESS: single
      (D) TOPOLOGY: linear (xi) SEQUENCE DESCRIPTION: SEQ ID NO:2:

CGCGAACTAT CCAGCTCGAG TGGGTGGTGA GC    32

(2) INFORMATION FOR SEQ ID NO:3:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (xi) SEQUENCE DESCRIPTION: SEQ ID NO:3:

GCACTAGTGA ATTCCCGGCT GTGAACGGGG ATTCGCCCG        39

(2) INFORMATION FOR SEQ ID NO:4:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO:4:

GCGTTTTCTT GCGAATTCGC TTTACCTTCA AAGGG        35